United States Patent
Ohiro et al.

(10) Patent No.: US 7,132,031 B2
(45) Date of Patent: Nov. 7, 2006

(54) PROCESS FOR MAKING A DISPOSABLE DIAPER

(75) Inventors: Masaya Ohiro, Kagawa-ken (JP); Akihisa Shiomi, Kagawa-ken (JP); Kyoko Ito, Kagawa-ken (JP); Kyota Saito, Kagawa-ken (JP); Akihide Ninomiya, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 2 days.

(21) Appl. No.: 10/751,480

(22) Filed: Jan. 6, 2004

(65) Prior Publication Data

US 2004/0194879 A1    Oct. 7, 2004

Related U.S. Application Data

(63) Continuation of application No. PCT/JP02/09233, filed on Sep. 10, 2002.

(30) Foreign Application Priority Data

Sep. 11, 2001   (JP)   ............................. 2001-275630

(51) Int. Cl.
*B32B 37/00* (2006.01)
*A61F 13/15* (2006.01)

(52) U.S. Cl. ..................... 156/270; 156/200; 156/204; 156/226; 156/227; 156/265; 156/302; 156/516; 156/519; 156/512; 156/270

(58) Field of Classification Search ................ 156/523, 156/265, 269, 270, 299, 302, 512, 219, 558, 156/559, 560, 200, 204, 226, 227, 516, 519
See application file for complete search history.

(56) References Cited

U.S. PATENT DOCUMENTS 3,874,386 A * 4/1975 Kozak ........................ 604/390
4,237,890 A * 12/1980 Laplanche .................. 604/390
6,328,725 B1 * 12/2001 Fernfors ..................... 604/391

FOREIGN PATENT DOCUMENTS

JP            5-39531        5/1993
JP          2000-502573      3/2000

* cited by examiner

*Primary Examiner*—Linda Gray
(74) *Attorney, Agent, or Firm*—Lowe Hauptman & Berner LLP

(57) ABSTRACT

In a process for making disposable diapers, a first web is continuously fed in its longitudinal direction. Tape fastener members extending in the longitudinal direction are fed to the first web so as to straddle respective lines corresponding to the side edges of the respective backsheets. Each of the tape fastener members has its longitudinally opposite end portions folded in a Z-shape or an inverted Z-shape. Top sections of these Z-shape and inverted Z-shape are coated on their undersides with a first self adhesive and bottom sections of these Z-shape and inverted Z-shape are coated on their undersides with a second self-adhesive. The tape fastener member is bonded to the first web by means of the second self-adhesive. The first web and the tape fastener members are simultaneously cut along the lines.

16 Claims, 13 Drawing Sheets

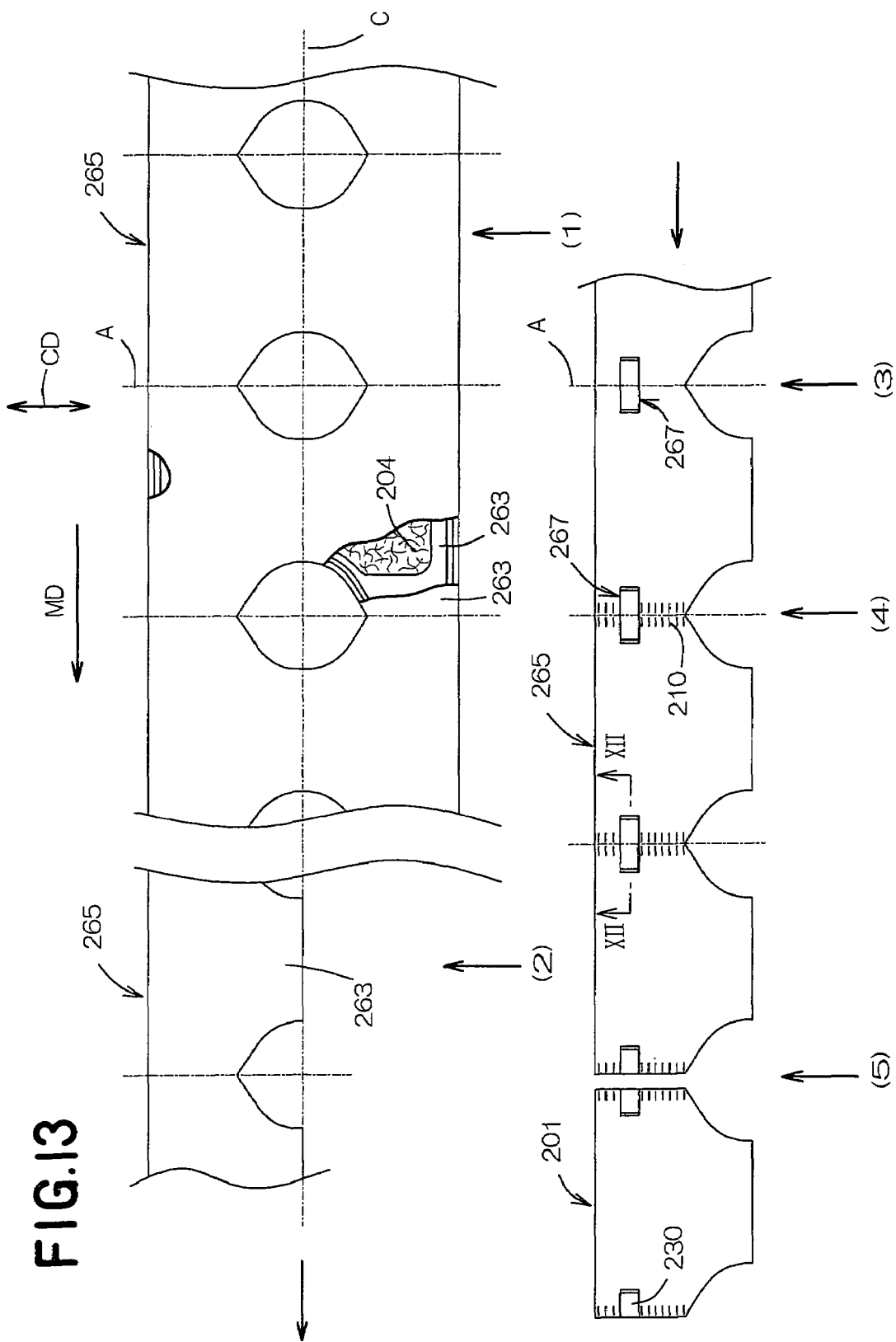

PROCESS FOR MAKING A DISPOSABLE DIAPER

This application is a continuation of WIPO Application No. PCT/JP02/09233 filed Sep. 10, 2002, which claims priority to Japanese Application No. 2001-275630 filed Sep. 11, 2001.

BACKGROUND OF THE INVENTION

This invention relates to a disposable diaper.

Japanese Utility Model Publication No. 1993-39531A discloses a pants-type wearing article. In this wearing article, tape fasteners folded in a Z-shape or an inverted Z-shape so as to be unfolded in a waist-surrounding direction when these tape fasteners are used are provided on a wearer's body facing surface of the rear waist region in the vicinity of the rear waist region's both side edges along which the rear waist region is overlaid and joined together with the front waist region. Top section of the tape fasteners corresponding to the top of the Z-shape is coated on its under surface with a self-adhesive. The tape fasteners may be unfolded and anchored to the wearing article at its appropriate positions to tighten the waist-surrounding dimension or to retain the used diaper in a rolled up state.

The invention described in the above-cited Publication certainly provides a pants-type wearing article having tape fasteners but not provides a process for making such a wearing article. While it is obviously possible to attach tape fasteners one by one to a wearing article, this invention aims to attach tape fasteners to a wearing article, for example, a disposable diaper in a remarkably efficient manner in the process for continuously making the wearing article.

SUMMARY OF THE INVENTION

According to this invention, there is provided a process for making a disposable diaper, the diaper having a wearer's body facing surface and a garment facing surface, front and rear ends extending in a transverse direction and a pair of side edges extending in a longitudinal direction, a front waist region, a rear waist region and a crotch region extending between the waist regions, and one of the front and rear waist regions of the garment facing surface being provided in vicinities of the side edges with tape fasteners folded so that the tape fasteners are unfolded in the transverse direction. This invention includes the steps of:
a) feeding continuously a first web in the transverse direction wherein the first web comprises a plurality of backsheets defining the garment facing surface having the pair of side edges and successively connected one to another along the side edges so as to be continuous in the transverse direction;
b) feeding tape fastener members to the first web fed in the step a), wherein each of the tape fastener members extending in the transverse direction has longitudinally opposite end portions and an intermediate portion extending between the opposite end portions, the opposite end portions being folded in a Z-shape or an inverted Z-shape, top sections of the Z-shape and the inverted Z-shape being coated on respective under surfaces with a first adhesive and bottom sections of the Z-shape and the inverted Z-shape being coated on respective under surfaces with a second adhesive, and bonding the tape fastener members by means of the second adhesive to the garment facing surface in one of the front and rear waist regions of the backsheets being contiguous one to another along the side edges in the first web so that the tape fastener members straddle the side edges, respectively; and
c) cutting the first web together with the tape fastener members along the side edges.

This invention may be implemented also in manners as follows:
(1) The first web is fed in the step a) in the condition that the first web is overlaid with a second web which is continuous in the transverse direction and destined to be a topsheet defining the wearer's body facing surface and liquid-absorbent cores arranged intermittently in the feeding direction of these first and second webs between these first and second webs.
(2) The first web is destined to define the garment facing surface of an open-type disposable diaper.
(3) The first web is destined to be the backsheet defining the garment facing surface of a pants-type disposable diaper and after the first web has been folded back along a line bisecting a vertical dimension of the first web so that a region of the first web destined to form the front waist regions and a region of the first web destined to form the rear waist regions are directly or indirectly overlaid each other, the folded back two regions are joined together at zones each having a desired width along lines to define the side edges of the diaper and thereafter the tape fastener members are bonded to the first web by means of the second adhesive on both sides of the respective zones of desired width so as to straddle the respective zones.

BRIEF DESCRIPTION OF THE DRAWINGS

FIG. 13 is a diagram similar to FIG. 11 illustrating a part of the process for making a pants-type disposable diaper.

DETAILED DESCRIPTION OF THE PREFERRED EMBODIMENTS

Details of the process for making a disposable diaper proposed by this invention will be more fully understood from the description given hereunder with reference to the accompanying drawings.

Figure 1:
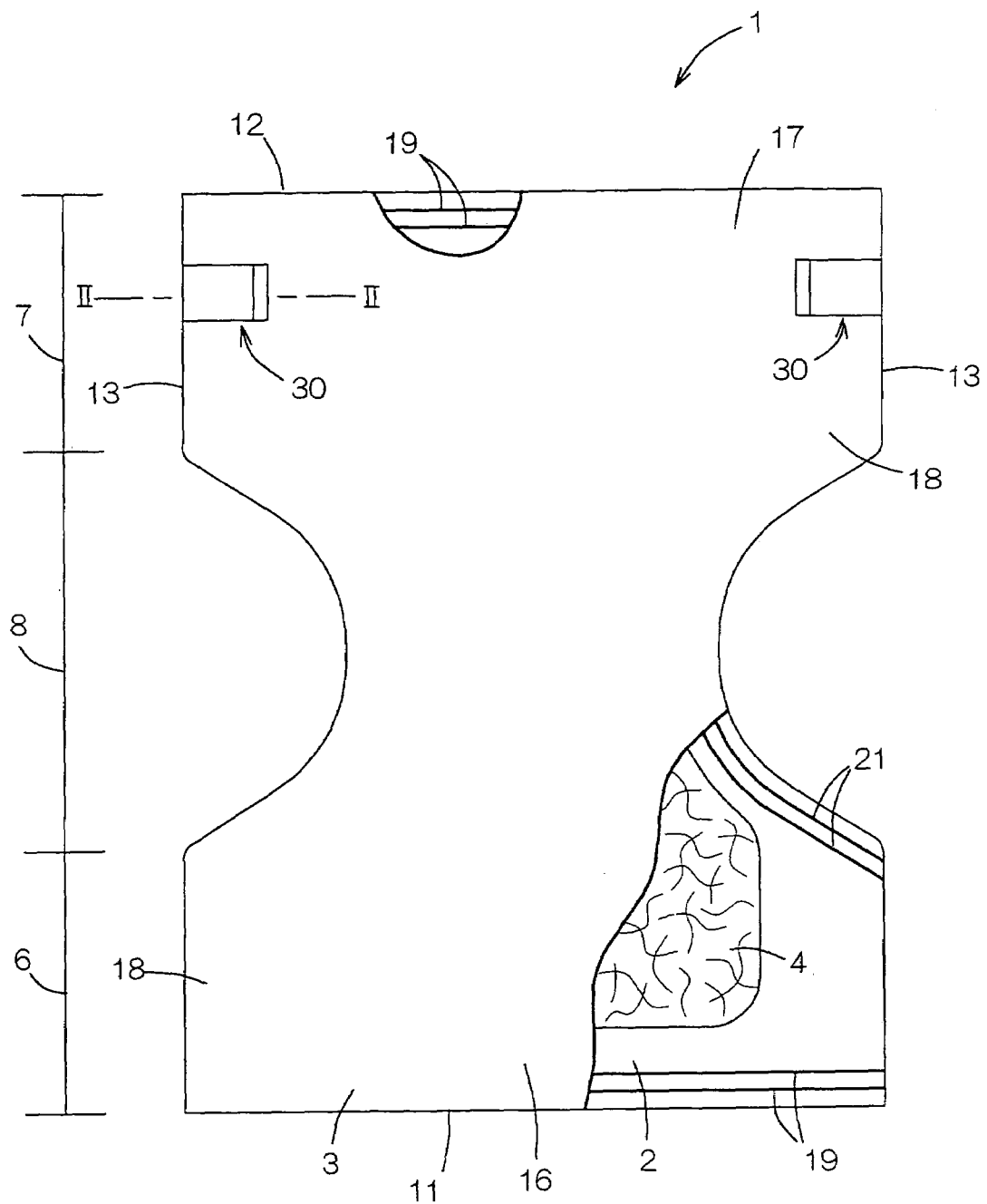
FIG. 1 is a partially cutaway plan view showing a disposable diaper.
Figure 2:
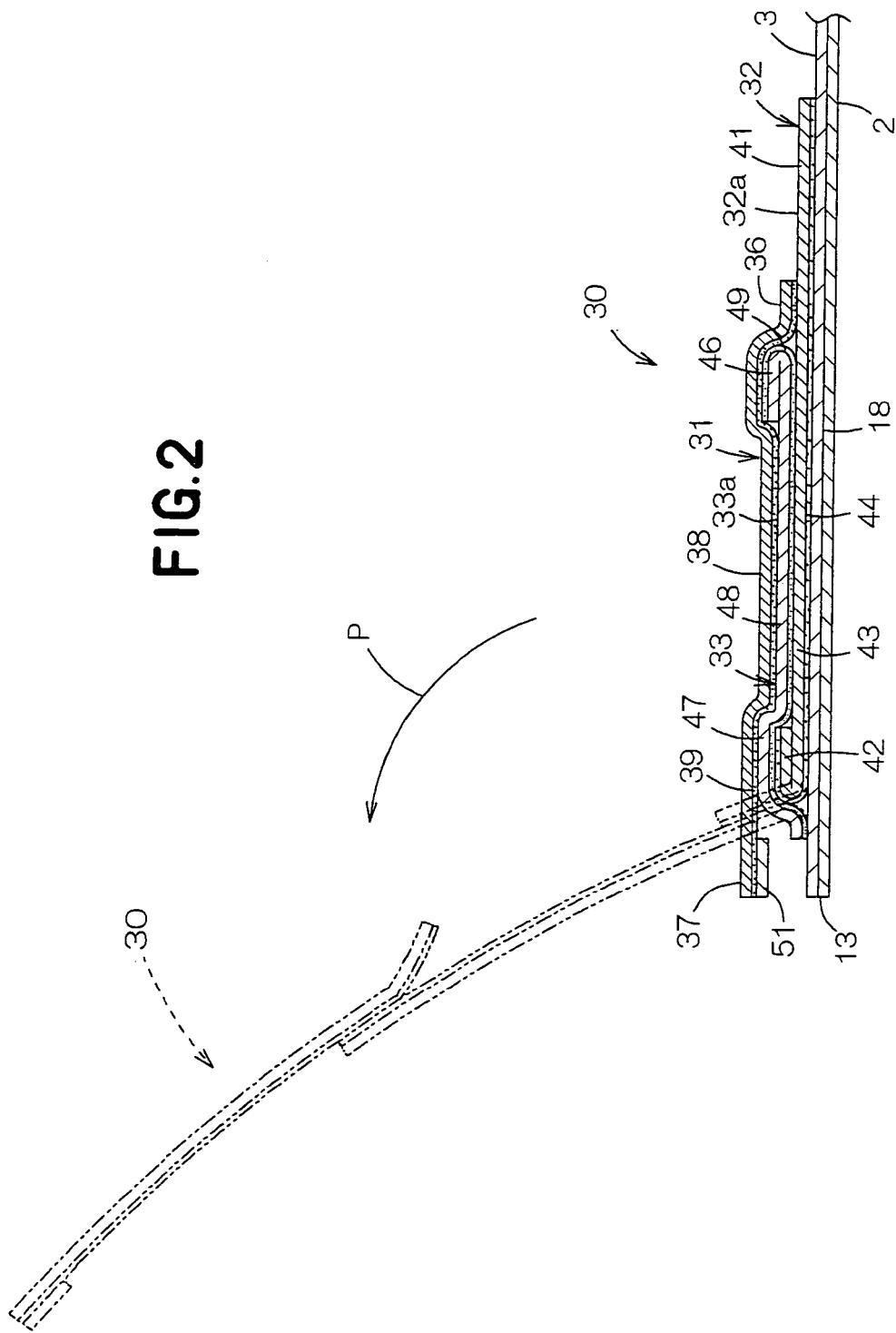
FIG. 2 is a cross-sectional view taken along a line II—II in FIG. 1.

FIG. 1 is a partially cut away plan view showing a disposable diaper 1 made by the process according to this invention and FIG. 2 is a cross-sectional view taken along a line II—II in FIG. 1. The diaper 1 comprises a liquid-pervious topsheet 2 facing a wearer's body, a liquid-impervious backsheet 3 facing a garment the wearer puts on and a liquid-absorbent core 4 interposed between these two sheets 2, 3. FIG. 1 is the plan view showing the diaper 1 with the backsheet 3 on the upper side and the topsheet 2 on the under side. The diaper 1 is contoured by front and rear ends 11, 12 extending in parallel to each other in a transverse direction and a pair of side edges 13 extending in parallel to each other in a longitudinal direction orthogonal to the transverse direction. The diaper 1 is composed of, in the longitudinal direction, a front waist region 6 put aside toward the front end 11, a rear waist region 7 put aside toward the rear end 12 and a crotch region 8 extending between these two waist regions 6, 7. In the crotch region 8, the side edges 13 curve inward. Respective portions of the top- and backsheets 2, 3 extend outward beyond a peripheral edge of the core 4 and are overlaid and joined together by means of a hot melt adhesive (not shown) to form a front flap 16, a rear flap 17 and side flaps 18. In the front flap 16 and the rear flap 17, waist-surrounding elastic members 19 are bonded in a stretched state to the inner surface of at least one of the top- and backsheets 2, 3. In the side flaps 18, thigh-surrounding elastic members 21 are stretched along the curved side edges 13 and bonded in this stretched state to the inner surface of at least one of the top- and backsheets 2, 3. In the rear waist region 7, tape fasteners 30 are attached to the backsheet 3 in the vicinity of the respective side edges 13. The tape fasteners 30 are folded so that these tape fasteners 30 may be unfolded outward beyond the respective side edges 13.

As viewed in FIG. 2, each of the tape fasteners 30 consists of a top tape section 31, a bottom tape section 32 and an intermediate tape section 33 lying between these top and bottom tape sections 31, 32. The top tape section 31 has an inner end portion 36, an outer end portion 37 and an intermediate portion 38 with respect to the diaper 1 and these portions 36–38 are coated on the under surfaces thereof with the first self-adhesive 39. The bottom tape section 32 also has an inner end portion 41, an outer end portion 42 and an intermediate portion 43 and these portions 41–43 are coated on the under surfaces thereof with the second self-adhesive 44. Similarly, the intermediate tape section 33 has an inner end portion 46, an outer end portion 47 and an intermediate portion 48 and these portions 46–48 are coated on the under surfaces thereof with the third self-adhesive 49. The inner end portion 36 of the top tape section 31 is temporarily fixed to an upper surface 32a of the bottom tape section 32 but firmly bonded to the folded upward inner end portion 46 of the intermediate tape section 33. The outer end portion 37 of the top tape section 31 extends outwardly of the diaper 1 beyond respective outer end portions of the bottom tape section 32 and the intermediate tape section 33. The first self-adhesive 39 coating the outer end portion 37 is covered with a small film strip 51. The intermediate portion 38 of the top tape section 31 is temporarily fixed to an upper surface 33a of the intermediate tape section 33. The bottom tape section 32 is firmly bonded over its substantially full length to an outer surface (upper surface as viewed in FIG. 2) of the backsheet 3. The outer end portion 42 of the bottom tape section 32 is folded upward and firmly bonded to the outer end portion 47 of the intermediate tape section 33 by means of the third self-adhesive 49. Except for the folded inner end portion 46 bonded to the top tape section 31 and the outer end portion 47 bonded to the outer end portion 42 of the bottom tape section 32, the intermediate tape section 33, i.e., the intermediate portion 48 thereof is temporarily fixed to the upper surface 32a of the bottom tape section 32. The top tape section 31, the intermediate tape section 33 and the bottom tape section 32 arranged in this manner form the continuous tape fastener folded in a Z-shape. The outer end portion 37 of the top tape section 31 may be held together with the small film strip 51 by fingers and pulled in the direction P outwardly of the diaper 1 to peel the temporarily fixed portions off one from another and thereby to unfold the tape fastener 30 as indicated by imaginary lines. In order to facilitate the first self-adhesive 39 to be peeled off from the bottom tape section 32 and the intermediate tape section 33 and/or in order to facilitate the third self-adhesive 49 to be peeled off from the bottom tape section 32, these tape sections 32, 33 may be coated with a suitable release agent such as silicone oil.

Figure 3:
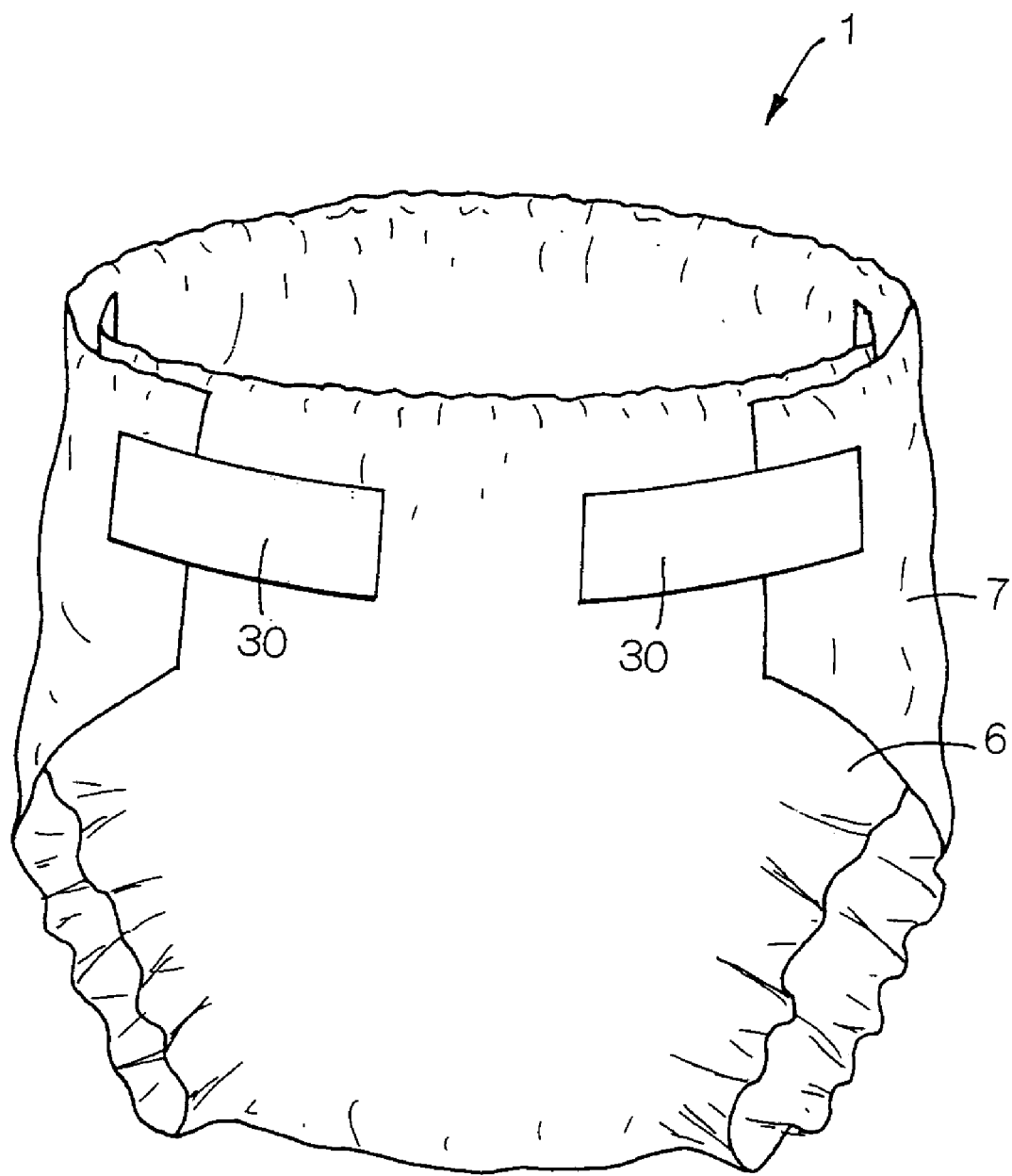
FIG. 3 is a diagram illustrating a manner in which the tape fasteners are used.
Figure 4:
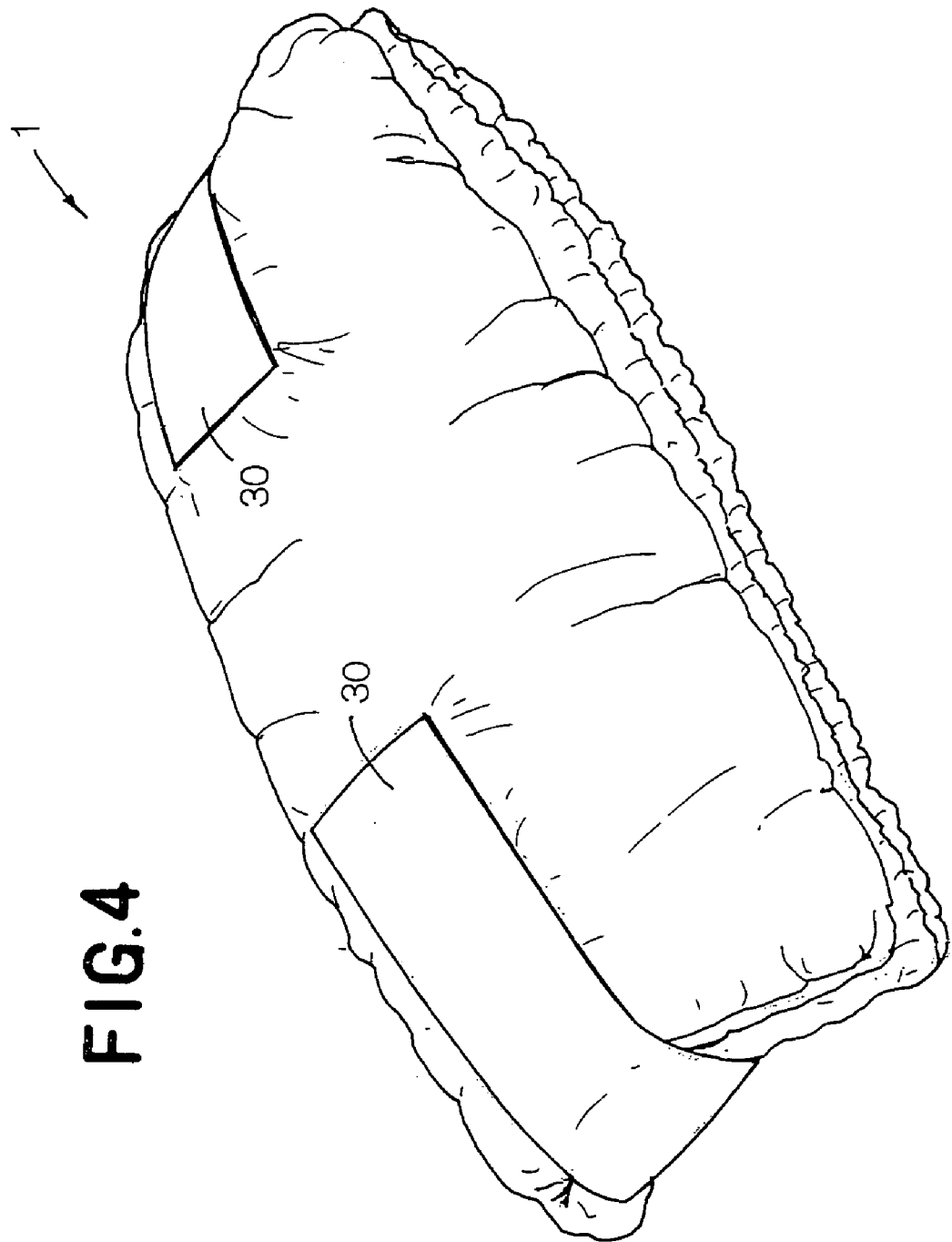
FIG. 4 is a diagram illustrating another manner in which the tape fasteners are used.

FIGS. 3 and 4 are diagrams illustrating manners in which the tape fasteners 30 are used. Referring to FIG. 3, the tape fasteners 30 are fully unfolded from the rear waist region 7 of the diaper 1 put on a wearer's body and detachably fixed to the front waist region 6. Referring to FIG. 4, the used diaper 1 has been rolled up and retained by the tape fasteners 30 in such a rolled up state. In this way, the tape fasteners 30 are useful not only to put the diaper 1 on the wearer's body but also to maintain the used diaper 1 in a rolled up state for disposal thereof.

Figure 5:
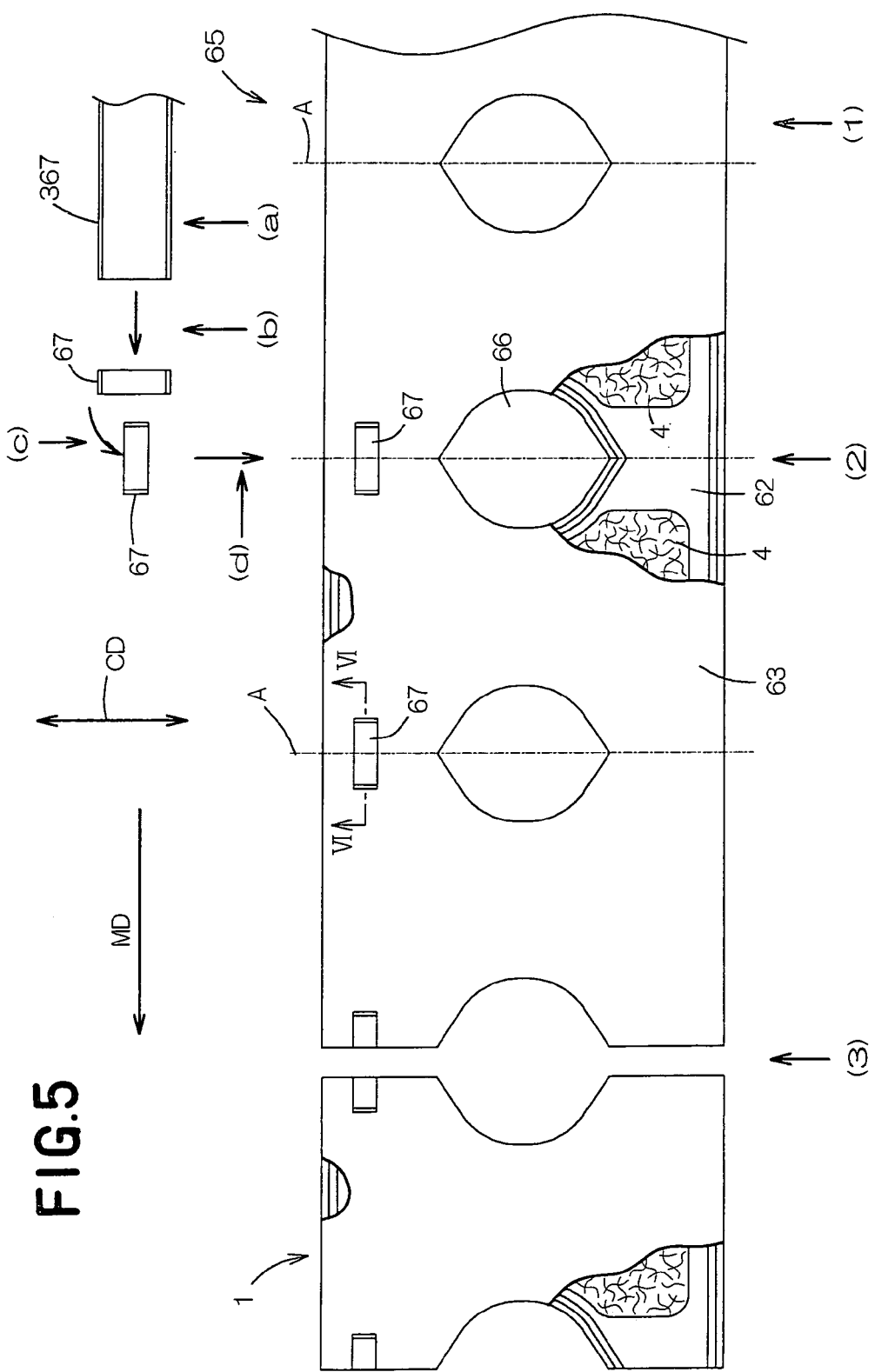
FIG. 5 is a diagram illustrating a part of the process for making a disposable diaper.

FIG. 5 is a diagram illustrating a part of the process for continuously making the diapers 1. In a series of steps (1)–(3) illustrated in the lower part of this diagram, an arrow pointing leftward indicates a machine direction MD. In the step (1), a continuous diaper 65 is fed in the machine direction MD. The continuous diaper 65 comprises continuous liquid-pervious web 62 destined to define the topsheet 2 of the diaper 1, continuous liquid-impervious web 63 placed on the web 62 and destined to define the backsheet 3 of the diaper 1 and the cores 4 intermittently arranged in the machine direction MD at given intervals and interposed between these webs 62, 63. These webs 62, 63 are overlaid and joined together by means of a hot melt adhesive (not shown) around the respective cores 4. Of the continuous diaper 65, a dimension in a direction CD orthogonal to the machine direction MD corresponds to a longitudinal dimension of the individual diaper 1 and an imaginary line A extending in the cross direction CD indicates a position representing each of the side edges 13 of the individual diaper 1. In these two webs 62, 63, a plurality of topsheets 2 are contiguous one to another along respective side edges 13 and a plurality of backsheets 3 are contiguous one to another along the respective side edges 13. The core 4 is placed between each pair of the adjacent imaginary lines A, A and the overlaid webs 62, 63 are cut out approximately in the middle of the imaginary line A to form a circular opening 66.

In the step (2), the tape fastener members 67 are fed from a series of steps (a)–(d) illustrated in the upper part of the diagram and these tape fastener members 67 are attached to the continuous diaper 65 traveling in the machine direction MD so that these tape fastener members 67 may straddle the respective imaginary lines A.

In the step (3), the continuous diaper 65 is cut along the imaginary lines A together with the taper fastener members 67 and the individual diapers 1 shown in FIG. 1 are obtained. Peripheral edges of the openings 66 formed in the continuous diaper 65 are destined to define the curved side edges 13 of the diaper 1 in its crotch region 8.

In a series of steps (a)–(d) illustrated in the upper part of FIG. 5, the tape fastener members 67 are prepared. In the step (a), continuous tape 367 destined to define the tape fastener members 67 is fed from the right hand toward the left hand as viewed in the diagram. In the step (b), the continuous tape 367 is cut in the transverse direction to obtain the individual tape fastener members 67. In the step (c), the tape fastener members 67 obtained in the step (b) are rotated by 90° so that the members 67 may extend in the machine direction MD. In the step (d), the tape fastener members 67 rotated in this manner are fed to the continuous diaper 65. It is possible to feed the continuous tape 367 in the cross direction CD rather than in the machine direction MD as illustrated and, in this case, the individual tape fastener members 67 obtained by cutting the continuous tape 367 are also fed in the cross direction CD to the continuous diaper 65.

Figure 6:
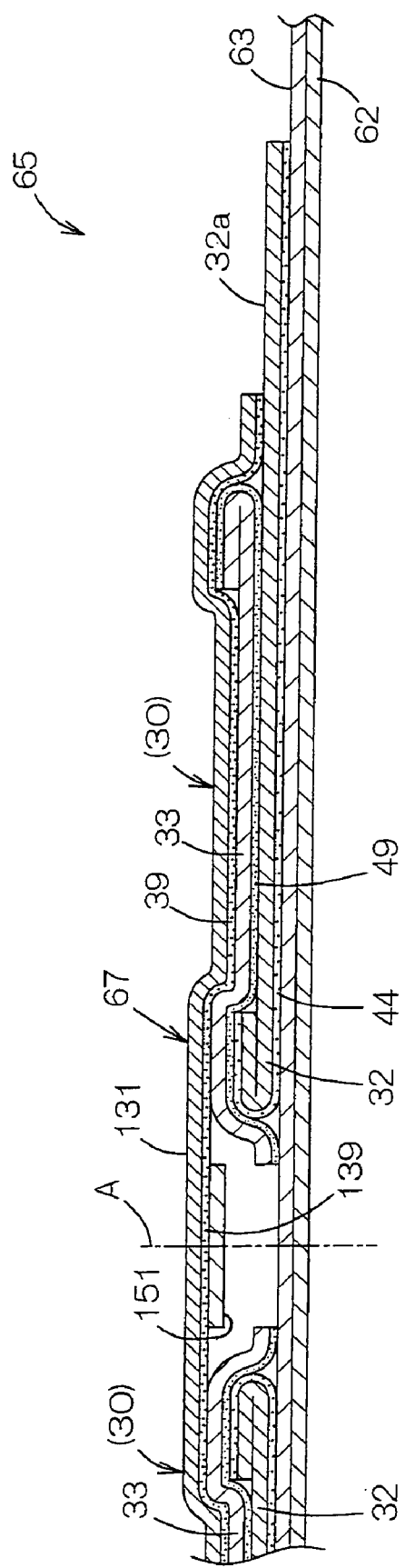
FIG. 6 is a cross-sectional view taken along a line VI—VI in FIG. 5.

FIG. 6 is a cross-sectional view of the continuous diaper 65 including the tape fastener members 67 shown in FIG. 5 as taken along a line VI—VI in FIG. 5. The tape fastener member 67 is symmetric about the imaginary line A, so the left half of the member 67 is not illustrated for the purpose of simplification. The tape fastener member 67 comprises a first tape section 131 straddling the imaginary line A and extending in the machine direction MD, the bottom tape section 32 bonded to the liquid-impervious web 63 on both sides of the imaginary line A by means of the second self-adhesive 44 and the intermediate tape section 33 temporarily fixed to the upper surface 32a of the bottom tape section 32 by means of the third self-adhesive 49. The first tape section 131 is temporarily fixed to the upper surface of the intermediate tape section 33 by means of a self-adhesive 139 and this self-adhesive 139 is covered with a small plastic film strip 151 in the vicinity of the imaginary line A. These continuous diaper 65 and tape fastener members 67 may be cut along the respective imaginary lines A to obtain the individual diapers 1 and the tape fasteners 30 attached thereto as shown in FIG. 1 wherein the liquid-pervious web 62 and the liquid-impervious web 63 respectively define the topsheet 2 and the backsheet 3. The first tape section 131, the self-adhesive 139 and the small plastic film strip 151 in the tape fastener member 67 may be cut along the imaginary line A to obtain the top tape section 31, the first self-adhesive 39 and the small plastic film strip 51 of the tape fastener 30 shown in FIG. 2. The bottom tape section 32 and the second self-adhesive 44 of the tape fastener member 67 respectively define the bottom tape section 32 and the second self-adhesive 44 of the diaper 1 and the intermediate tape section 33 and the third self-adhesive 49 respectively define the intermediate tape section 33 and the third self-adhesive 49 of the diaper 1. Referring to FIG. 6, of two tape fasteners 30 obtained from one and same tape fastener member 67, the tape fastener 30 lying on the right side of the imaginary line A—A is folded in a Z-shape and the tape fastener 30 lying on the left side is folded in an inverted Z-shape.

Such a process for continuously making the individual diapers 1 characterized in that the continuous diaper 65 is cut together with the tape fastener members 67 is more advantageous than the process of well known art according to which the tape fasteners 30 are separately prepared and attached to the diapers 1 one by one. The process according to this invention enables steps of cutting base material for the tape fasteners 30 to be eliminated by one step.

Figure 7:
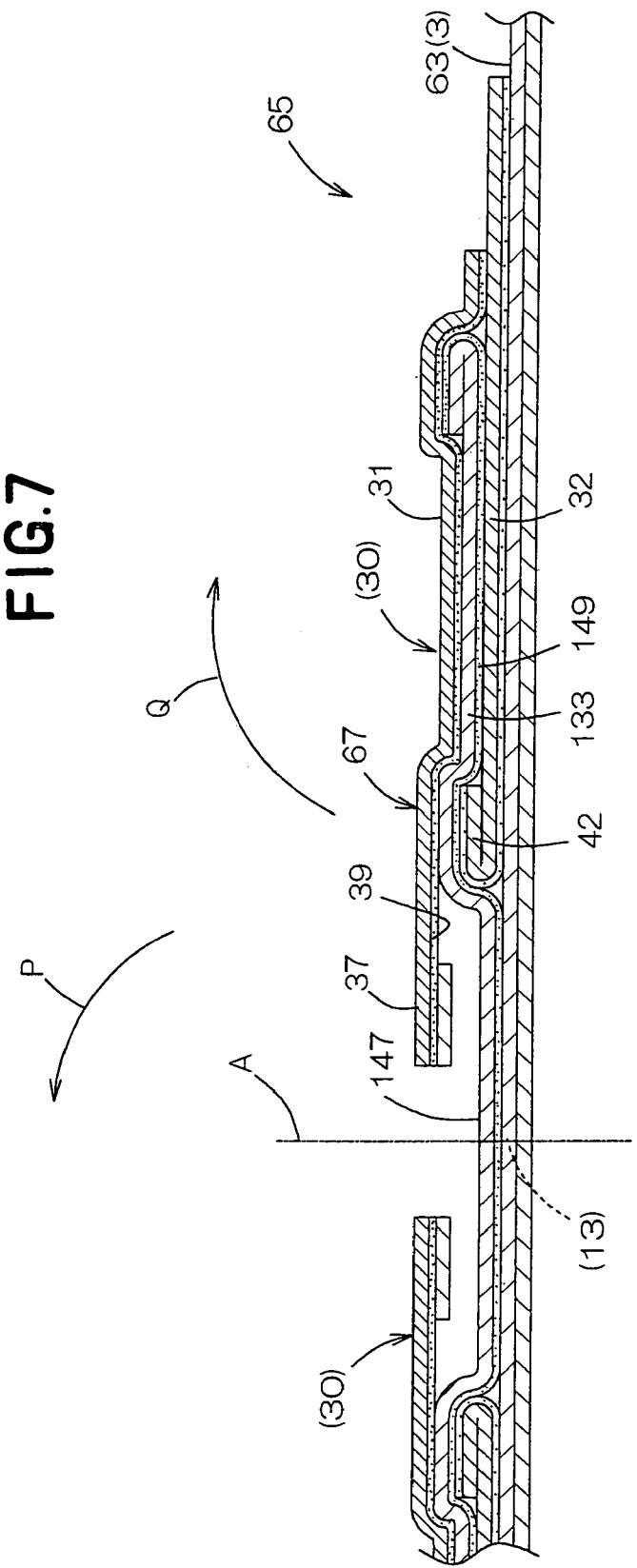
FIG. 7 is a cross-sectional view similar to FIG. 6 illustrating another embodiment of the tape fastener member.

FIG. 7 is a diagram similar to FIG. 6 illustrating another embodiment of this invention. The tape fastener member 67 used in this continuous diaper 65 comprises the top tape section 31, the bottom tape section 32 and a second tape section 133 interposed between these two tape sections 31, 32 wherein the second tape section 133 extends beyond the imaginary line A. The tape fastener member 67 may be cut together with the continuous diaper 65 along the imaginary line A to form the tape fasteners 30 on both sides of the imaginary line A similarly to the case of the tape fastener member 67 in FIG. 6. The top tape section 31 in this tape fastener member 67 and the first self-adhesive 39 applied on the under surface of this tape section 31 function in the same manner as the top tape section 31 and the first self-adhesive 39 applied to the under surface of this tape section 31 shown in FIG. 2. The bottom tape section 32 in the tape fastener member 67 and the second self-adhesive 44 applied on the under surface of this section 32 function also in the same manner of those in FIG. 2. While the second tape section 133 and a self-adhesive 149 applied on the under surface of the second tape section 133 function in the same manner as the intermediate tape section 33 and the third self-adhesive 49 in FIG. 2, a portion 147 of the second tape section 133 extending beyond the outer end portion 42 of the bottom tape section 32 to the imaginary line A is longer than the portion 47 of the tape fastener 30 in FIG. 2 and firmly bonded to the liquid-impervious web 63. In the diaper 1 using the second tape section 133, the tape fastener 30 may be pulled leftward in the direction P as viewed in FIG. 7 with the outer end portion 37 of the top tape section 31 held by fingers to unfold the top tape section 31, the bottom tape section 32 and the second tape section 133 in the same manner as the tape fastener 30 in FIG. 2. It should be understood that the portion 147 of the second tape section 133 remains bonded to the backsheet 3 defined by the second web 63. In the tape fastener 30 according to this embodiment, the portion 147 bonded to the backsheet 3 over a relatively large area is effective to prevent a force tending to peel the bottom tape section 32 off from the backsheet 3 from acting upon the bottom tape section 32.

Figure 8:
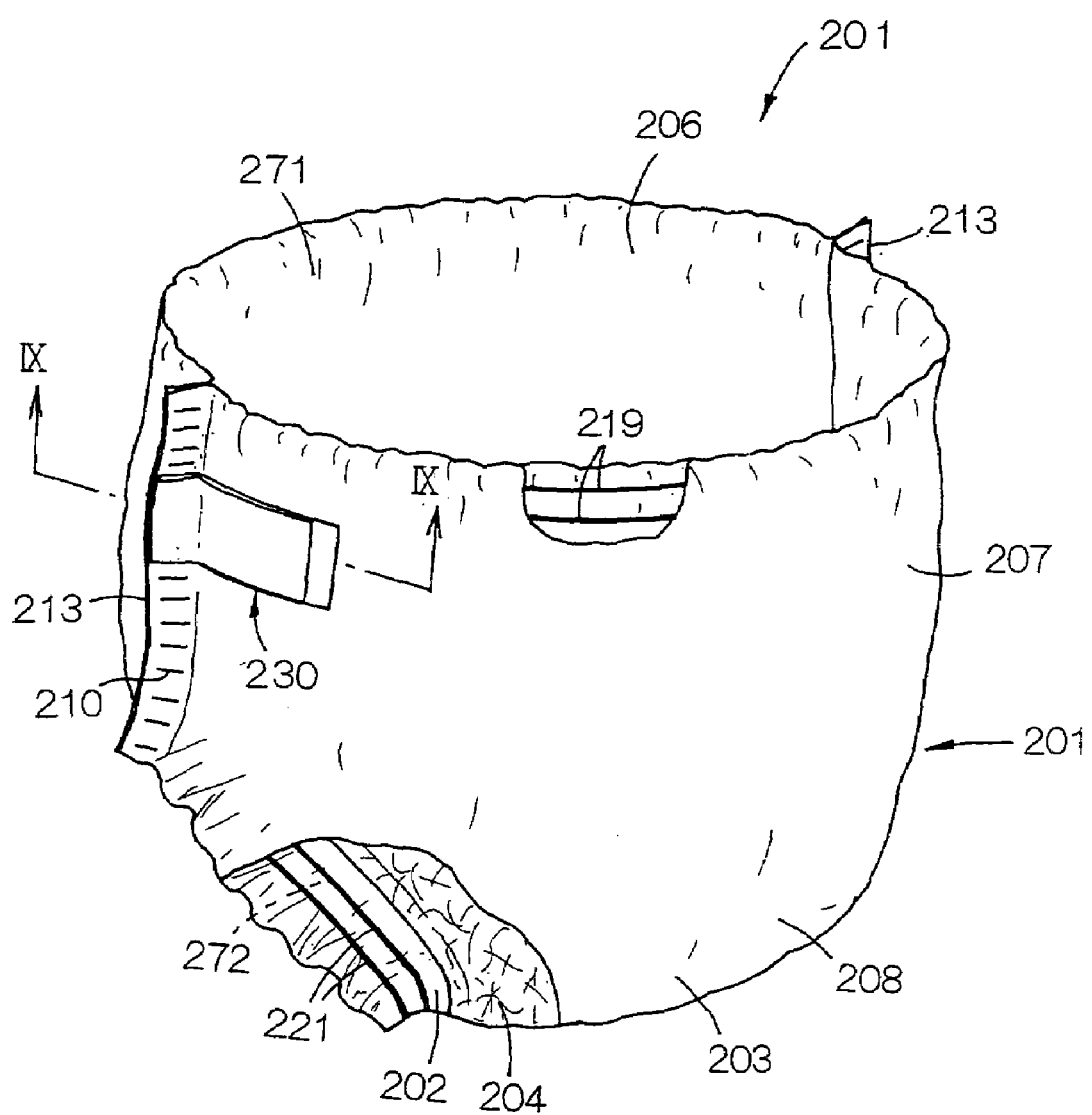
FIG. 8 is a partially cutaway perspective view showing a pants-type disposable diaper.

FIG. 8 is a partially cutaway perspective view showing a pants-type disposable diaper 201 made by the process according to this invention. The diaper 201 comprises a liquid-pervious topsheet 202, a liquid-impervious backsheet 203 and a liquid-absorbent core 204 disposed between these two sheets 202, 203 so as to configure a front waist region 206, a rear waist region 207 and a crotch region 208. The front and rear waist regions 206, 207 are overlaid together in the vicinity of transversely opposite side edges 213 thereof and joined together at bonding zones 210 arranged intermittently in the longitudinal direction of the diaper 201 so as to define a waist-hole 271 and a pair of leg-holes 272. A waist-surrounding elastic member 219 is attached in a stretched state to a peripheral edge portion of the waist-hole 271 and thigh-surrounding elastic members 221 are attached in a stretched state to peripheral edge portions of the leg-holes 272. The rear waist region 207 is provided with tape fasteners 230 in the vicinity of the respective side edges 213.

Figure 9:
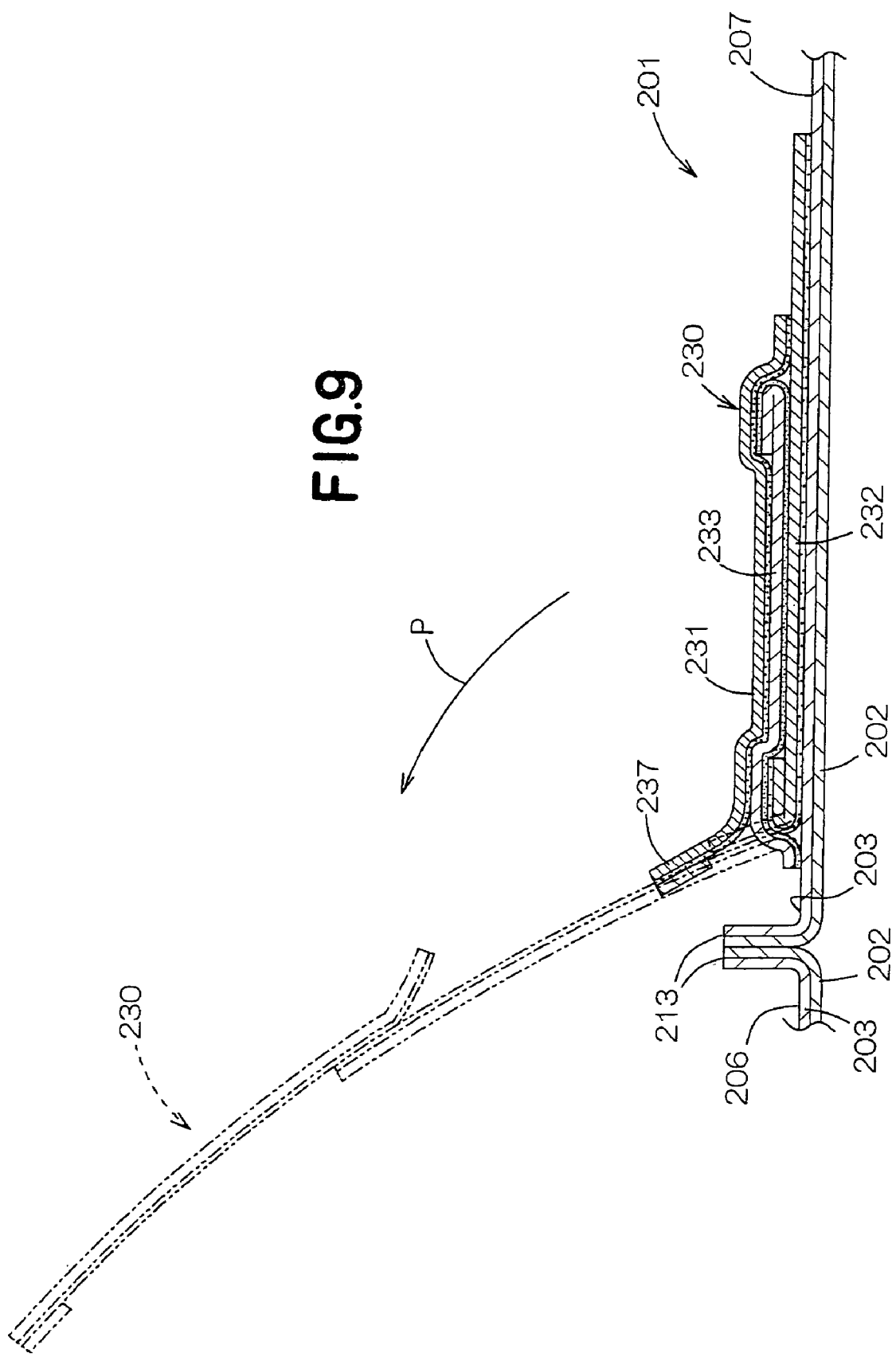
FIG. 9 is a cross-sectional view taken along a line IX—IX in FIG. 8.

FIG. 9 is a cross-sectional view taken along a line IX—IX in FIG. 8. In the diaper 201, the front and rear trunk regions 206, 207 are overlaid together in the vicinity of the side edges 213 and the top- and backsheets 202, 203 are joined together at the bonding zones 210. The tape fastener 230 is identical to the tape fastener 30 in FIG. 2, so the regions of the tape fastener 230 are designated by the reference numerals added 200 to the reference numerals of the corresponding tape fastener 30. The tape fastener 230 can be unfolded with the outer end portion 237 of the top tape section 231 held by fingers so as to extend in the direction P beyond the side edge 213 of the rear waist region 207 to the front waist region 206.

Figure 10:
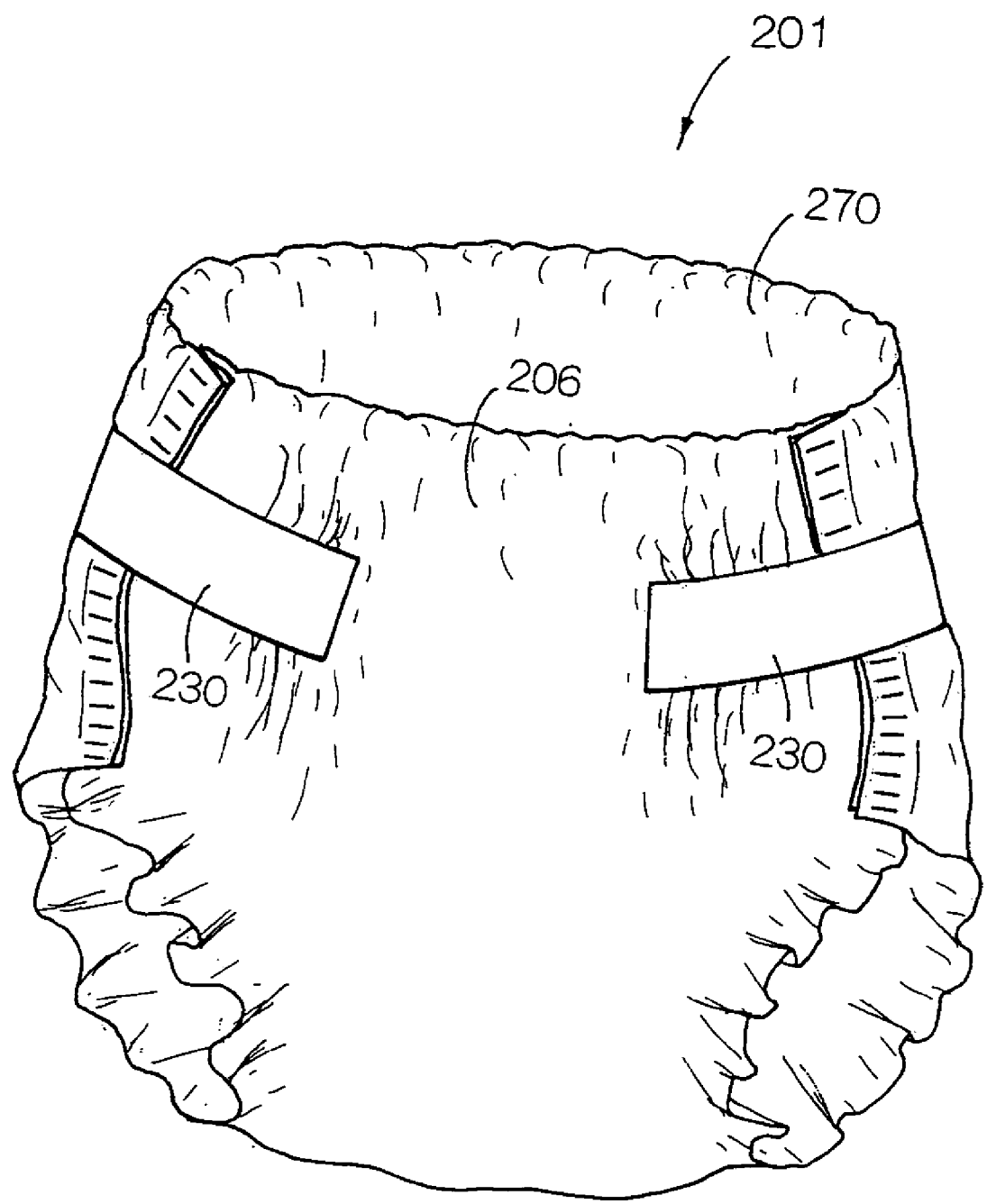
FIG. 10 is a perspective view of a pants-type disposable diaper illustrating a manner in which the tape fasteners are used.

FIG. 10 is a perspective view of a pants-type disposable diaper 201 illustrating a manner in which the tape fasteners 230 are used. In the case of the diaper 201 shown in FIG. 10, the front waist region 206 is pulled toward the rear waist region 207 using the tape fasteners 230 so that the diaper 201 may be tucked to alleviate overabundance in the waist-surrounding direction. This tape fastener 230 also is useful to retain the used diaper in a rolled up state as the tape fastener 30 of FIG. 5 is.

Figure 11:
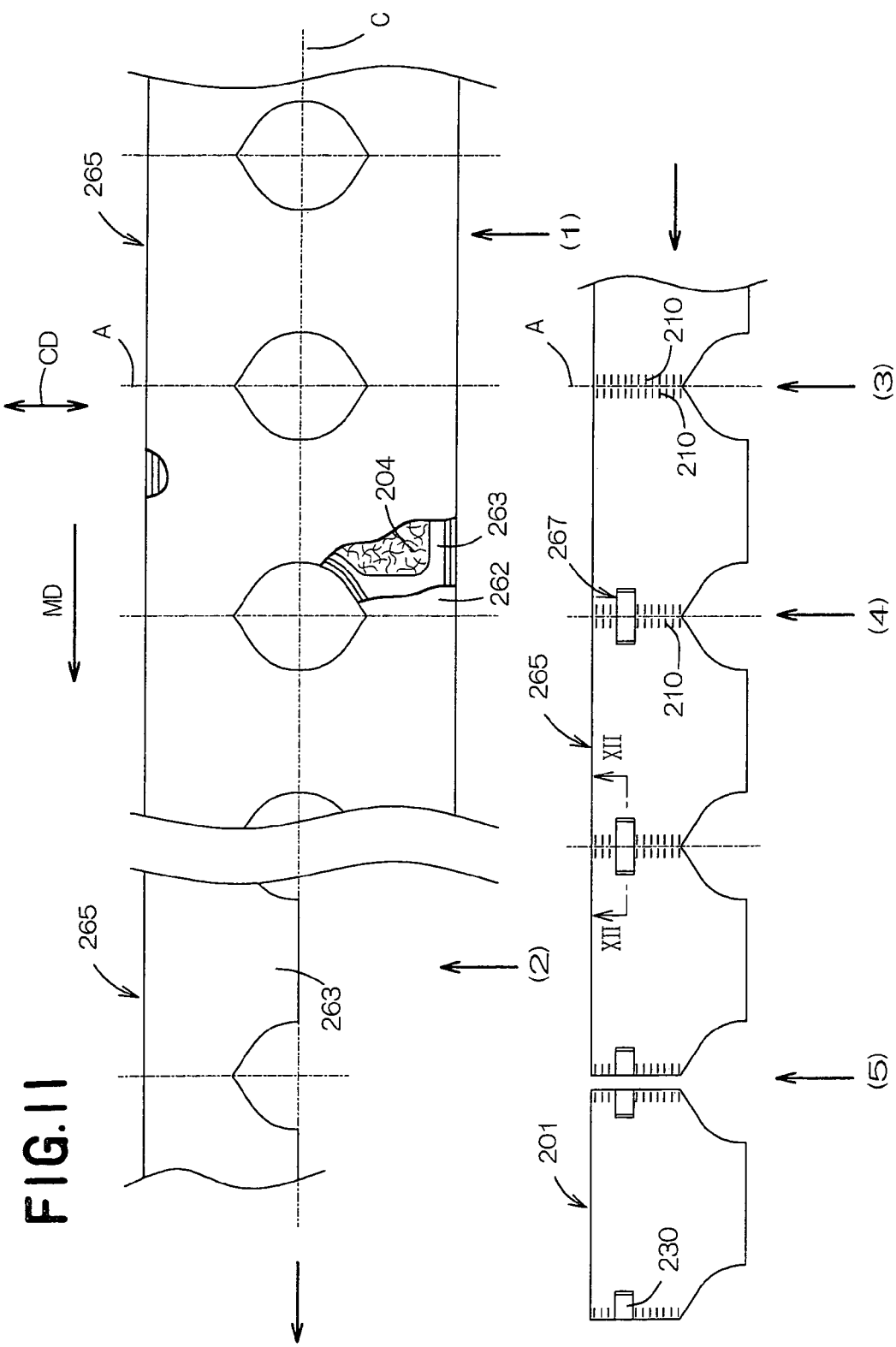
FIG. 11 is a diagram illustrating a part of the process for making a pants-type disposable diaper.

FIG. 11 is a diagram illustrating a part of the process for continuously making the diaper 201 having the tape fasteners 230. In the step (1), continuous diaper 265 destined to be the pants-type diapers 201 is fed from the right hand toward the left hand as viewed in FIG. 11, i.e., in the machine direction MD. The continuous diaper 265 is similar to the continuous diaper 65 of FIG. 5 except that a continuous liquid-pervious web 262 is placed on a continuous liquid-impervious web 263 and the cores 204 are interposed between these webs 262, 263. In the step (2), the continuous diaper 265 is folded back along the center line C bisecting a dimension of the continuous diaper 265 in the cross direction CD crossing the machine direction MD with the liquid-pervious web 262 inside. In the step (3), the bonding zones 210 are formed on both sides of the imaginary line A extending in the cross direction CD in the middle between each pair of the adjacent cores 204, 204 so that two layers of the continuous diaper 265 formed by folding back may be intermittently joined together. In the step (4), the tape fastener members 267 are fed so as to straddle the bonding zones 210 in the machine direction MD and bonded to the liquid-impervious web 263 on both sides of the bonding zones 210. In the step (5), the continuous diaper 265 is cut along the imaginary lines A together with the tape fastener members 267 and the individual pants-type diapers 201 are obtained.

Figure 12:
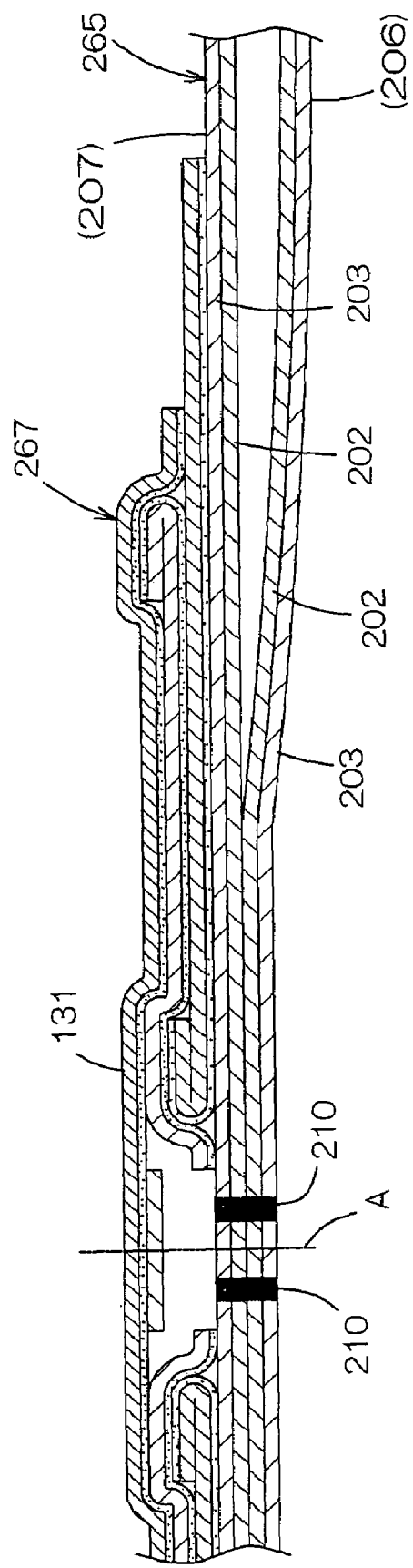
FIG. 12 is a cross-sectional view taken along a line XII—XII in FIG. 11.

FIG. 12 is a cross-sectional view taken along a line XII—XII in FIG. 11. On both sides of the respective imaginary lines A extending across the continuous diaper 265, the liquid-pervious web 262 and the liquid-impervious web 263 destined to form the front waist regions 206, on one hand, and the liquid-pervious web 262 and the liquid-impervious web 263 destined to form the rear waist regions 207, on the other hand, are welded together in the bonding zones 210. Similarly to the tape fastener member 67 shown by FIG. 5, the tape fastener member 267 has the uppermost first tape section 131 straddling the bonding zones 210 formed on both sides of the imaginary line A. This tape fastener member 267 may be cut along the imaginary line A to obtain the tape fastener 230 shown in FIG. 10.

FIG. 13 is a diagram similar to FIG. 11 illustrating a part of the process for making the pants-type disposable diaper 201 comprising steps different from those in the process illustrated by FIG. 11. Referring to FIG. 13, in the step (3), the tape fastener members 267 are fed to the continuous diaper 265 so as to straddle the respective imaginary lines A and bonded to the liquid-impervious web 263. In the step (4), the bonding zones 210 are formed on both sides of the respective imaginary lines A. In the case that the liquid-pervious web 262 and the liquid-impervious web 263 are made of a thermoplastic material having a relatively low softening temperature such as polyethylene or polypropylene and the tape fastener member 267 is made of a thermoplastic material having a relatively high softening temperature such as polyester, the liquid-pervious web 262 and the liquid-impervious web 263 may be heat-sealed above the tape fastener member 267 to form the bonding zones 210 and thereby to obtain the pants-type diaper 201 having the arrangement similar to that shown by FIG. 12.

It is possible without departing from the scope of this invention to use, in the process illustrated by FIGS. 11 and 13, the tape fastener member 67 shown in FIG. 6 instead of the tape fastener member 267 shown in FIG. 12. In the process illustrated by FIG. 11, it is possible without departing from the scope of this invention to directly joined two layers of the folded back liquid-impervious web 263 without interposition of the liquid-pervious web 262 in the bonding zones 210. The liquid-pervious web 62, 262 and the liquid-impervious web 63, 263 are preferably made of a heat-sealable sheet material containing thermoplastic synthetic resin over 50 wt %. This invention may be implemented in a manner that the tape fasteners 30, 230 are attached to the front waist region 6, 206 instead of attaching them to the rear waist region 7, 207 as for the diaper 1, 201 as illustrated.

The process according to this invention for making the disposable diapers is primarily characterized in that the continuous diaper is cut together with the tape fastener members and thereby the individual diapers are obtained. Thus the time and labor required to prepare the tape fasteners for production of the disposable diaper can be alleviated.

What is claimed is:

1. A process of making disposable diapers each having
   inner and outer surfaces adapted to face toward and away from a wearer, respectively.
   front and rear ends extending in a transverse direction and a pair of side edges extending in a longitudinal direction,
   a front waist region, a rear waist region and a crotch region extending between said waist regions, and
   one of said front and rear waist regions of said outer surface being provided in vicinities of said side edges with folded tape fasteners which are unfoldable in said transverse direction,
   said process comprising the steps of:
   feeding continuously a web in a machine direction which defines the transverse direction of the diapers to be made, wherein said web comprises backsheets of the diapers arranged side-by side and has a surface defining the outer surface of the diapers;
   providing tape fastener members each having, in said machine direction, longitudinally opposite end portions and an intermediate portion extending between said opposite end portions, said opposite end portions being folded in a Z-shape or an inverted Z-shape, top sections of said Z-shape and said inverted Z-shape being coated on undersides thereof with a first adhesive and bottom sections of said Z-shape and said inverted Z-shape being coated on undersides thereof with a second adhesive;
   bonding said tape fastener members by means of said second adhesive to said surface of said web in said one of said front and rear waist regions of said backsheets of the diapers so that said tape fastener members straddle cutting lines which are located between adjacent ones of the diapers and define the side edges of the diapers; and
   cutting said web together with said tape fastener members along said cutting lines to separate the individual diapers from said web:
   said process further comprising, prior to said bonding, folding said web along a line bisecting a width of said web so that a first region of said web destined to form the front waist regions of the diapers and a second region of said web destined to form the rear waist regions of the diapers overlay each other; and joining the folded first and second regions together in joining zones on opposite sides of the cutting lines destined to define said side edges of said diapers;

wherein, in said bonding, said tape fastener members are bonded to said web by means of said second adhesive on opposite sides of respective said joining zones so as to straddle respective said joining zones.

2. The process of claim 1, wherein the diapers being cut from said web are pant diapers.

3. A process of making disposable diapers each having inner and outer surfaces adapted to face toward and away from a wearer, respectively, front and rear ends extending in a transverse direction and a pair of side edges extending in a longitudinal direction, a front waist region, a rear waist region and a crotch region extending between said waist regions, and one of said front and rear waist regions of said outer surface being provided in vicinities of said side edges with folded tape fasteners which are unfoldable in said transverse direction, said process comprising the steps of:

feeding continuously a web in a machine direction which defines the transverse direction of the diapers to be made, wherein said web comprises backsheets of the diapers arrange side-by side and has a surface defining the outer surface of the diapers;

providing tape fastener members each having, in said machine direction, longitudinally opposite end portions and an intermediate portion extending between said opposite end portions, said opposite end portions being folded in a Z-shape or an inverted Z-shape, top sections of said Z-shape and said inverted Z-shape being coated on undersides thereof with a first adhesive and bottom sections of said Z-shape and said inverted Z-shape being coated on undersides thereof with a second adhesive;

bonding said tape fastener members by means of said second adhesive to said surface of said web in said one of said front and rear waist regions of said backsheets of the diapers so that said tape fastener members straddle cutting lines which are located between adjacent ones of the diapers and define the side edges of the diapers; and cutting said web together with said tape fastener members along said cutting lines to separate the individual diapers from said web:

wherein, in each of said tape fastener members being provided in said providing, each of the Z-shape and inverted Z-shape further comprises, in addition to the top and bottom sections, a middle section located between the top and bottom sections; and said first adhesive releasably bonds the top section to the middle section at a first end of the middle section, and permanently bonds the top section to the middle section at an opposite, second end of the middle section.

4. The process of claim 3, wherein, in each of said tape fastener members being provided in said providing, the middle section is coated on a underside thereof with a third adhesive; and said third adhesive releasably bonds the middle section to the bottom section at the second end of the middle section, and permanently bonds the middle section to the bottom section at the first end of the middle section.

5. The process of claim 4, wherein, in each of said tape fastener members being provided in said providing, the second end of the middle section comprises a folded portion which has the third adhesive facing upwardly and being permanently bonded to the first adhesive of the top section; and the bottom section comprises, in a region corresponding to the first end of the middle section, another folded portion which has the second adhesive facing upwardly and being permanently bonded to the third adhesive of the middle section.

6. A process of making disposable diapers each having inner and outer surfaces adapted to face toward and away from a wearer, respectively, front and rear ends extending in a transverse direction and a pair of side edges extending in a longitudinal direction, a front waist region, a rear waist region and a crotch region extending between said waist regions, and one of said front and rear waist regions of said outer surface being provided in vicinities of said side edges with folded tape fasteners which are unfoldable in said transverse direction, said process comprising the steps of:

feeding continuously a web in a machine direction which defines the transverse direction of the diapers to be made, wherein said web comprises backsheets of the diapers arranged side-by side and has a surface defining the outer surface of the diapers;

providing tape fastener members each having, in said machine direction, longitudinally opposite end portions and an intermediate portion extending between said opposite end portions, said opposite end portions being folded in a Z-shape or an inverted Z-shape, top sections of said Z-shape and said inverted Z-shape being coated on undersides thereof with a first adhesive and bottom sections of said Z-shape and said inverted Z-shape being coated on undersides thereof with a second adhesive;

bonding said tape fastener members by means of said second adhesive to said surface of said web in said one of said front and rear waist regions of said backsheets of the diapers so that said tape fastener members straddle cutting lines which are located between adjacent ones of the diapers and define the side edges of the diapers; and cutting said web together with said tape fastener members along said cutting lines to separate the individual diapers from said web;

wherein said bonding comprises permanently bonding the tape fastener members to said web.

7. A process of making disposable diapers, said process comprising:

feeding continuously a web in a machine direction, wherein said web comprises backsheets of a plurality of diapers arranged side-by side with intended cutting lines located between adjacent said diapers, and said web further has a surface defining an outer surface of the diapers;

providing tape fastener members each having, in said machine direction, longitudinally opposite end portions and an intermediate portion extending between said opposite end portions, said opposite end portions respectively comprising two folded tape fasteners for two adjacent said diapers on said web;

bonding the opposite end portions of said tape fastener members to said surface of said web, wherein the intermediate portion of each of said tape fastener members extends across one of said intended cutting lines; and simultaneously cutting said web and the tape fastener members along said cutting lines to obtain the individual diapers having the folded tape fasteners.

8. The process according to claim 7, wherein said web being continuously fed comprises a first layer defining the backsheets and the outer surface of the diapers, a second layer defining a topsheet and the inner surface of the diapers, and a plurality of liquid-absorbent cores arranged intermittently in the machine direction between the first and second layers.

9. The process according to claim 7, further comprising, prior to said bonding, folding said web along a line bisecting a width of said web so that a first region of said web intended to form front waist regions of the diapers and a second region of said web intended to form rear waist regions of the diapers overlay each other; and joining the folded first and second regions together in joining zones on opposite sides of the cutting lines intended to define longitudinal side edges of the diapers;

wherein, in said bonding, the opposite end portions of said tape fastener members are bonded to said web on opposite sides of respective said joining zones and the intermediate portions of said tape fastener members straddle respective said joining zones.

10. The process according to claim 7, wherein said bonding comprises permanently bonding the opposite end portions of the tape fastener members to said web.

11. The process of claim 7, wherein, in each of said tape fastener members being provided in said providing, the opposite end portions are folded in a Z-shape or an inverted Z-shape, each said Z-shape or inverted Z-shape comprising a top section, a bottom section that is bonded to said web in said bonding, and a middle section located between the top and bottom sections; and the intermediate portion is made integrally with and connects the top sections of the Z-shape and inverted Z-shape of the opposite end portions.

12. The process of claim 7, wherein, in each of said tape fastener members being provided in said providing, the opposite portions are folded in a Z-shape or an inverted Z-shape, each said Z-shape or inverted Z-shape comprising a top section, a bottom section that is bonded to said web in said bonding, and a middle section located between the top and bottom sections; and the intermediate portion is made integrally with and connects the bottom sections of the Z-shape and inverted Z-shape of the opposite end portions.

13. The process of claim 7, wherein, in each of said tape fastener members being provided in said providing, the opposite end portions are folded in a Z-shape or an inverted Z-shape, each said Z-shape or inverted Z-shape comprising a top section, a bottom section that is bonded to said web in said bonding, and a middle section located between the top and bottom sections; and the top section is releasably bonded to the middle section at a first end of the middle section, and permanently bonded to the middle section at an opposite, second end of the middle section.

14. The process of claim 13, wherein, in each of said tape fastener members being provided in said providing, the middle section is releasably bonded to the bottom section at the second end of the middle section, and permanently bonded the bottom section at the first end of the middle section.

15. The process of claim 14, wherein, in each of said tape fastener members being provided in said providing, the top, bottom and middle sections are coated on undersides thereof with first, second and third adhesives, respectively, said second adhesive bonding the respective Z-shape or inverted Z-shape to said web in said bonding;

the second end of the middle section comprises a folded portion which has the third adhesive facing upwardly and being permanently bonded to the first adhesive of the top section; and the bottom section comprises, in a region corresponding to the first end of the middle section, another folded portion which has the second adhesive facing upwardly and being permanently bonded to the third adhesive of the middle section.

16. A process of making disposable diapers each having inner and outer surfaces adapted to face toward and away from a wearer, respectively, front and rear ends extending in a transverse direction and a pair of side edges extending in a longitudinal direction, a front waist region, a rear waist region and a crotch region extending between said waist regions, and one of said front and rear waist regions of said outer surface being provided in vicinities of said side edges with folded tape fasteners which are unfoldable in said transverse direction, said process comprising the steps of:

feeding continuously a web in a machine direction which defines the transverse direction of the diapers to be made, wherein said web comprises backsheets of the diapers arranged side-by side and has a surface defining the outer surface of the diapers;

providing tape fastener members each having, in said machine direction, longitudinally opposite end portions and an intermediate portion extending between said opposite end portions, said opposite end portions being folded in a Z-shape or an inverted Z-shape, top sections of said Z-shape and said inverted Z-shape being coated on undersides thereof with a first adhesive and bottom sections of said Z-shape and said inverted Z-shape being coated on undersides thereof with a second adhesive;

bonding said tape fastener members by means of said second adhesive to said surface of said web in said one of said front and rear waist regions of said backsheets of the diapers so that said tape fastener members straddle cutting lines which are located between adjacent ones of the diapers and define the side edges of the diapers; and cutting said web and said tape fastener members along said cutting lines to separate the individual diapers from said web;

said process further comprising, prior to said bonding, folding said web along a line bisecting a width of said web so that a first region of said web destined to form the front waist regions of the diapers and a second region of said web destined to form the rear waist regions of the diapers overlay each other; and joining the folded first and second regions together in joining zones on opposite sides of the cutting lines destined to define said side edges of said diapers;

wherein, in said bonding, said tape fastener members are bonded to said web by means of said second adhesive on opposite sides of respective said joining zones so as to straddle respective said joining zones.

* * * * *